United States Patent [19]
van Aelst et al.

[11] Patent Number: 5,877,156
[45] Date of Patent: Mar. 2, 1999

[54] THROMBIN INHIBITORS

[75] Inventors: Sjoert Folkert van Aelst, Megen; Anton Egbert Peter Adang, Eindhoven; Adrianus Petrus Antonius de Man, Loon op Zand; Jacobus Albertus Maria Peters, Oss, all of Netherlands

[73] Assignee: Akzo Nobel, N.V., Arnhem, Netherlands

[21] Appl. No.: 63,484

[22] Filed: Apr. 21, 1998

[30] Foreign Application Priority Data

Apr. 24, 1997 [EP] European Pat. Off. .............. 97201217

[51] Int. Cl.$^6$ .............................. A61K 38/06; C07K 5/08; C07K 5/087
[52] U.S. Cl. ............................................... 514/18; 530/331
[58] Field of Search .................................. 530/331; 514/18

[56] References Cited

U.S. PATENT DOCUMENTS 5,523,308  6/1996  Costanzo et al. ........................ 514/317
5,614,499  3/1997  Bylund et al. ............................ 514/19

FOREIGN PATENT DOCUMENTS 8-20597     1/1996  Japan .
WO 97/17363 5/1997  WIPO .
WO 98/07308 2/1998  WIPO .

OTHER PUBLICATIONS

Database WPI XP002060823, Jan. 23, 1996.

*Primary Examiner*—Jeffrey E. Russel
*Attorney, Agent, or Firm*—Mary E. Gormley

[57] ABSTRACT

The invention relates to a thrombin inhibitor of the formula:

$$R^1NH-CHR^2-C(O)-A-B-X \qquad (I)$$

wherein $R^1$ is -(1–6C)alkylene-COOH or -(1–6C)alkylene-CONH$_2$;

$R^2$ is a side chain of a hydrophobic D-amino acid;

A is an amino acid selected from proline, optionally containing a second heteroatom selected from N, O, or S, and optionally substituted with (1–6C)alkyl, (1–6C)alkoxy or halogen, 2-azetidine carboxylic acid, pipecolinic acid, octahydroindole-2-carboxylic acid or valine;

B is lysine, 3- or 4-aminocyclohexylglycine or ω-(1–6C)alkyl-lysine; and

X is a heterocycle selected from 2-thiazole, 2-thiazoline, 2-benzothiazole, 2-oxazole, 2-oxazoline, 2-benzoxazole, 2-imidazole and 2-benzimidazole, which heterocycles are optionally substituted with one or more substituents selected from (1–6C)alkyl, (1–6C)alkoxy, oxo, hydroxy, halogen, phenyl, —C(O)O—(1–6C)alkyl and amido; or a pharmaceutically acceptable salt thereof. The compounds of the invention have anticoagulant activity and can be used in treating or preventing thrombin-related diseases.

26 Claims, No Drawings

THROMBIN INHIBITORS

FIELD OF THE INVENTION

The invention relates to thrombin inhibitors, pharmaceutical compositions containing the same, as well as the use of said inhibitors for treating and preventing thrombin-related diseases.

BACKGROUND OF THE INVENTION

Thrombin is a member of the class of the serine proteases. Serine proteases are enzymes which, amongst other things, play an important role in the blood coagulation cascade. Other members of this class of proteases are for example trypsin, factors VIIa, IXa, Xa, XIa, XIIa, and protein C.

Thrombin is the serine protease which regulates the last step in the coagulation cascade. The prime function of thrombin is the cleavage of fibrinogen to generate fibrin monomers, which form an insoluble gel by cross-linking. In addition, thrombin regulates its own production by activating factors V and VIII earlier in the cascade. It also has important actions at the cellular level, where it acts on specific receptors to cause platelet aggregation, endothelial cell activation and fibroblast proliferation. Thus throinbin has a central regulatory role in haemostasis and thrombus formation. Since inhibitors of thrombin may have a wide range of therapeutical applications, extensive research has been performed in this area.

In the development of synthetic inhibitors of sernie proteases, and more specifically of thrombin, the interest in small synthetic peptides that are recognized by proteolytic enzymes in a manner similar to that of natural substrates, has increased. As a result, new peptide-like inhibitors have been prepared, such as the transition state inhibitors of thrombin.

The search for more effective and more selective thrombin inhibitors continues unabated in order to obtain thrombin inhibitors which can be administered in lower dosages and which have fewer and less severe side effects.

Furthermore, special attention is paid to oral bioavailability. Potent intravenous thrombin inhibitors are clinically effective in acute care settings requiring the treatment of thrombin-related diseases. However, particularly the prevention of thrombin-related diseases such as myocardial infarct, thrombosis and stroke require long-term therapy, preferably by orally dosing of an anticoagulant.

Many of the peptide-like thrombin inhibitors disclosed in prior publications are based on the sequence -D-Phe-Pro-Arg-, see for example compounds as disclosed by Brady et al. [Bioorganic & Medical Chemistry, 3 (1995), 1063–78]. Thrombin inhibitors may also contain lysine side chains instead of arginine, Such as other inhibitors disclosed by Brady et al., and further by Jones et al. [J. Enzyme Inhibition, 9 (1995), 43–60] and Lewis et al. [Thrombosis and Haemostasis, 74(4) (1995), 1107–12]. Also thrombin inhibitors having an aminocyclohexyl moiety instead of 2 lysine or arginine side chain are known [WO 94/25051]. From these and other references [e.g. U.S. Pat. No. 5,523, 308] further a number of variations at the C-terminus of these peptide-like thrombin inhibitors is known. The developments in this field have already improved the understanding of how to modulate the biological properties of this type of thrombin inhibitor. However, although great effort is being spent on finding selective thrombin inhibitors having good oral bioavailability, there are still few transition state thrombin inhibitors known in the art which fulfill these requirements.

SUMMARY OF THE INVENTION

It has now been found that thrombin inhibitors of the formula:

$$R^1NH-CHR^2-C(O)-A-B-X \qquad (I)$$

wherein $R^1$ is -(1–6C)alkylene-COOH or -(1–6C)alkylene-$CONH_2$;

$R^2$ is a side chain of a hydrophobic D-amino acid;

A is an amino acid selected from proline, optionally containing a second heteroatom selected from N, O, or S, and optionally substituted with (1–6C)alkyl, (1–6C) alkoxy or halogen, 2-azetidine carboxylic acid, pipecolinic acid, octahydroindole-2-carboxylic acid or valine;

B is lysine, 3- or 4-aminocyclohexylglycine or ω-(1–6C) alkyl-lysine, and

X is a heterocycle selected from 2-thiazole, 2-thiazoline, 2-benzothiazole, 2-oxazole, 2-oxazoline, 2-benzoxazole, 2-imidazole and 2-benzimidazole, which heterocycles are optionally substituted with one or more substituents selected from (1–6C)alkyl, (1–6C) alkoxy, oxo, hydroxy, halogen, phenyl, -C(O)O-(1–6C) alkyl and amido;

or a pharmaceutically acceptable salt thereof, are potent and selective thrombin inhibitors. Further, compounds of the invention show good bioavailability after oral administration.

The compounds of the present invention are usefuil for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

DETAILED DESCRIPTION OF THE INVENTION

Preferred thrombin inhibitors according to this invention are the compounds wherein B is lysine. Particularly preferred are compounds wherein A is proline. The most preferred compounds of the invention are those wherein $R^1$ is —$CH_2COOH$. Further preferred compounds according to the invention are those wherein X is a substituted heterocycle.

The term (1–6C)alkylene means a branched or unbranched alkylene group having 1 to 6 carbon atoms, such as —$(CH_2)_m$—and m is 1 to 6,—$CH(CH_3)$—, —$CH(CH_3)$—$(CH_2)$—, etc. The preferred alkylene group is methylene.

The term (1–6C)alkyl means a branched or unbranched alkyl group having 1 to 6 carbon atoms, such as methyl, ethyl, isopropyl, n-butyl, t-butyl, isopentyl, and the like. Preferred are (1–4C)alkyl groups.

The term (1–6C)alkoxy means an alkoxy group having 1–6 carbon atoms, the alkyl moiety of which having the meaning as previously defined.

The term halogen means fluorine, chlorine, bromine or iodine.

The term hydrophobic D-amino acid means a D-amino acid having a hydrophobic side chain being (3–8C) cycloalkyl, (6–14C)aryl or (1–6C)alkyl, which alkyl group may optionally be substituted with one or more (3–8C) cycloalkyl groups or (6–14C)aryl groups. The term (3–8C) cycloalkyl means a cycloalkyl group having 3–8 carbon atoms, being cyclopropyl, cyclobutyl, cyclopentyl, cyclohexyl, cycloheptyl or cyclo-octyl. A (6–14C)aryl group is an aromatic moiety of 6 to 14 carbon atoms, which may further contain one or more hetero atoms, such as N, S, or O. Examples of aryl groups are phenyl, pyridinyl, naphthyl, tetrahydronaphthyl, and the like. The hydrophobic side chain may optionally be substituted with one or more substituents, such as hydroxy, halogen, trifluorometllyl, $-OSO_2CF_3$, (1–4C)alkyl (for instance methyl or ethyl), (1–4C)alkoxy (for instance methoxy), phenyloxy, benzyloxy, and the like. Preferred hydrophobic D-amino acids are cyclohexylalanine, cyclo-octylalanine, phenylalanine, naphthylalanine, tyrosine, 3,3-diphenylalanine, norleucine and leucine.

The invention further includes a process for preparing a compound of formula I, including coupling of suitably protected amino acids or amino acid analogs, followed by removing the protective groups.

The compounds according to formula I may be prepared in a manner conventional for such compounds. To that end, suitably Nα protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tert-butyloxycarbonyl group (Boc), benzyloxycarbonyl (Cbz) group and substituted analogs or the base-labile 9-fluorenyl-methyloxycarbonyl (Fmoc) group. The Cbz group can also be removed by catalytic hydrogenation. Other suitable amino protective groups include Nps, Bmv, Bpoc, Msc, etc. A good overview of amino protective groups is given is given in The Peptides, Analysis, Synthesis, Biology, Vol. 3 E. Gross and J. Meienhofer, Eds., (Academic Press, New York, 1981). Protection of carboxyl groups can take place by ester formation e.g. base-labile esters like methyl- or ethylesters, acid labile esters like tert-butylesters, or hydrogenolytically-labile esters like benzylesters. Protection of the side chain function of lysine, 3- or 4-aminocyclohexylglycine or ω-(1–6C)alkyl-lysine may be accomplished by using the aforementioned groups. Activation of the carboxyl group of the suitably protected amino acids or peptides can take place by the azide, mixed anhydride, active ester, or carbodiimide method, especially with the addition of catalytic and racemization-suppressing compounds like 1-hydroxybenzotriazole, N-hydroxysucciniminde, 3-hydroxy-4-oxo-3,4-dihydro-1,2,3-benzotriazine, N-hydroxy-5-norbornene-2,3-dicarboximide. See, e.g. The Peptides, Analysis, Synthesis, Biology (see above) and Pure and Applied Chem. 59(3), 331–344 (1987).

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharnaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further explained by reference to the following illustrative Examples.

Et=ethyl
Bzl=benzyl
Boc=tert-butyloxycarbonyl
Cbz=benzyloxycarbonyl
Cha=cyclohexylalaninyl
Pro=prolinyl
Lys=lysinyl
Acg=4-aminocyclohexyl glycinyl

EXAMPLE 1

2-(N-Carboxymethyl-D-cyclohexylalanyl-prolyl-lysinyl)-4,5-dimethylthiazole (a) H-D-Cha-OMe.HCl To cold (−20° C.) and dry methanol (195 ml) was added dropwise thionylchloride (28 ml). H-D-ChaOH.HCl (40 g) was added and the reaction mixture was heated under reflux for 5 h. The mixture was concentrated in vacuo and coevaporated with methanol (3 times). The residue was crystallized from methanol/diethylether yielding H-D-Cha-OMe.HCl as a white crystalline powder (40.9 g, 95.8%).

TLC: $R_f$=0.66, silica gel, n-butanol/acetic acid/water=10/1/3 v/v %.

(b) N-(t-Butyloxycarbonylmethyl)-D-Cha-OMe t-Butyl-bromo acetate (36 g) was added to a stirred solution H-D-Cha-OMe.HCl (40.9 g) in 400 ml of acetonitrile. The pH of the mixture was adjusted to 8.5 with diisopropylethylamine. The mixture was stirred for 16 hours at room temperature and evaporated in vacuo. The residue was dissolved in dichloromethane and the solution was washed with water, dried on sodium sulfate and evaporated in vacuo. Chromatography over silica gel in heptane/ethyl acetate 9/1 (v/v) gave 64 g of N-(t-butyloxycarbonylmethyl)-D-Cha-OMe.

TLC: $R_f$=0.25, silica gel, ethyl acetate/heptane=1/1 v/v %.

(c) N-(t-Butyloxycarbonylmethyl)-N-Boc-D-Cha-OMe

The pH of a solution of N-(t-butyloxycarbonylmethyl)-D-Cha-OMe (64 g) and di-t-butyl dicarbonate (40.3 g) was adjusted to 8.5 with diisopropylethylamine. The mixture was stirred for 16 hours at room temperature. The solvent was removed in vacuo. Dichloromethane and water were added to the residue. The organic layer was separated, washed with cold 1N hydrogen chloride, water, 5% sodium hydrogen carbonate and water. The organic layer was dried on sodium sulfate and the filtrate was evaporated to an amorphous solid of N-(t-Butyloxycarbonylmethyl)-N-Boc-D-Cha-OMe with a yield of 59.6 g.

TLC: $R_f$=0.50, silica gel, ethyl acetate/heptane=1/1 v/v %.

(d) N-(t-Butyloxycarbonylmethyl)-N-Boc-D-Cha-OH

A solution of N-(t-Butyloxycarbonylmethyl)-N-Boc-D-Cha-OMe (59.6 g) in 900 ml of dioxane/water=9/1 (v/v) was treated with sufficient 6N sodium hydroxide to keep the pH at 12 for 6 hours at room temperature. After acidification, the mixture was poured into water and was extracted with dichloromethane. The organic layer was washed with water and was dried on sodium sulfate. The filtrate was evaporated and yielded 54 g of N-(t-Butyloxycarbonylmethyl)-N-Boc-D-Cha-OH.

TLC: $R_f$=0.60, silica gel, dichloromethane/methanol=9/1 v/v %.

(e) N-(t-Butyloxycarbonylmethyl)-N-Boc-D-Cha-Pro-OBzl

To a cold (0° C.) solution of N-(t-Butyloxycabonylmethyl)-N-Boc-D-Cha-OH (13.5 g) in N,N-dimethyl formamide (150 ml) were successively added 1-hydroxy benzotriazole (7.09 g), dicyclohexyl carbodiimide (7.61 g), H-Pro-OBzl.HCl (9.31 (g) and triethylamine (6 ml). The mixture was stirred at 0° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 5% sodium hydrogen carbonate, water, 3% citric acid and brine, dried over sodium sulfate and concentrated in vacuo. The residue was chromatographed on silica gel in heptane/ethyl acetate=3/1 (v/v) as eluent. The fractions containing N-(t-Butyloxycarbonylmethyl)-N-Boc-D-Cha-Pro-OBzl were pooled and evaporated. Yield: 15 g.

TLC: $R_f$=0.70, silica gel, heptane/ethyl acetate=1/1 v/v %.

(f) N-(t-Butyloxycarbonylmethyl)-N-Boc-D-Cha-Pro-OH

10% palladium on charcoal (750 mg) was added to a solution of N-(t-Butyloxy-carbonylmethyl)-N-Boc-D-Cha-Pro-OBzl (15 g) in methanol (150 ml). The mixture was hydrogenated at atmospheric pressure at room temperature for 1 hour. The palladium catalyst was removed by filtration and the solvent was removed by evaporation at reduced pressure yielding 11.2 g N-(t-Butyloxycarbonylmethyl)-N-Boc-D-Cha-Pro-OH.

TLC: $R_f$=0.65, silica gel, ethyl acetate/pyridine/acetic acid/water=213/20/6/11 v/v %.

(g) 2-Bromo-4,5-dimetlhylthiazole

To a cold (0° C.) suspension of copper(I)bromide (2.6 g) in acetonitril (100 ml) was dropwise added isoamylnitrite (3.27 ml). The reaction mixture was heated to 65° C. and a solution of 2-amino-4,5-dimethylthiazole (2.5 g) in acetonitril (25 ml) was added dropwise. The mixture was stirred for 10 min at 65° C. and 30 min at room temperature. The mixture was poured into ethyl acetate (500 ml) and washed with 1M hydrogenchloride-solution, water, 5% sodium bicarbonate solution and brine. The ethyl acetate layer was dried over sodium sulphate and concentrated in vacuo. The residue was chormatographed on silica gel and dichloromethane as eluent. Fractions containing 2-bromo-4,5-dimethylthiazole were pooled and evaporated. Yield: 1.2 g.

TLC: $R_f$=0.75, silica gel, heptane/ethyl acetate=3/1 v/v %.

(h) 2-tert-butyloxycarbonylamino-6-benzyloxycarbonylainino-hexanoic acid N,O-dimethylhydroxylamide (=Boc-Lys(Cbz)-N(CH$_3$)(OCH$_3$))

Boc-Lys(Cbz)-OH (25 g) was dissolved in dichloromethane (500 ml). O,N-dimethylhydroxylamine.HCl (6.73 g) and TBTU were added and the pH was adjusted to pH 8 by adding triethylamine. The reaction mixture was stirred for 1 h at room temperature. The mixture was washed successively with cold 2M hydrogen chloride solution, water, 5% sodium bicarbonate solution and water. The organic layer was dried over sodium sulphate, filtered and evaporated. The residue was purified by chormatography on silica (eluent: heptane/ethyl acetate=3/2 v/v %). To yield 28.4 g Boc-Lys(Cbz)-N(CH$_3$)(OCH$_3$).

TLC: $R_f$=0.95, silica gel, dichloromethane/methanol=95/5 v/v %.

(i) 2-(N-Boc(N-Cbz))-lysinyl)-4,5-dimethylthiazole

To a cold (−78° C.), stirred solution of 1.3M n-butyllithium in hexane (4.8 ml), was added, dropwise, a solution of 2-bromo-4,5-dimethylthiazole (1.2 g) in diethylether (10 ml). After the solution had been stirred at −78° C. for 10 min, a solution of Boc-Lys(Cbz)-N(CH$_3$)(OCH$_3$) (0.81 g) in dry tetrahydrofuran (20 ml) was added slowly. The mixture was stirred at −78° C. for 1 h, then 2% aqueous citric acid/solution was added. The mixture was allowed to warm to room temperature and the layers were separated. The organic layer was washed with water and brine, dried over sodium sulphate, filtered and evaporated. The residue was purified by chromatography on silica (eluent: ethyl acetate/heptane=2/3 v/v %) to yield 344 mg of the title compound.

TLC: $R_f$=0.81, silica gel, ethyl acetate/heptane=3/1 v/v %.

(i) 2-(N-benzyloxycarbonyl)-lysinyl-4 5-dimethylthiazole 2-(N-Boc(N-benzyloxycarbonyl)-lysinyl)-(4,5-dimethyl)-thiazole (330 mg) was dissolved in 50% trifluoroacetic acid/dichloromethane (10 ml) and stirred for 1 h at room temperature. The crude amine was isolated as a yellow oil in quantitative yield after removal of the solvent by evaporation, and used immediately to prepare TLC: $R_f$=0.45, silica gel, ethyl acetate/pyridine/acetic acid/water=163/20/6/11 v/v %.

(k) 2-(N-(t-Butyloxycarbonylmethyl)-N-Boc-D-cyclohexylalanyl-prolyl-lysinyl(Cbz))-4,5-dimethylthiazole N-(t-Butyloxycarbonylmethyl)-N-Boc-D-Cha-Pro-OH (325 mg) was dissolved in dry dimethylformamide (5 ml). After addition of ethyl diisopropyl amine (234 µl), the reaction mixture was placed under nitrogen and cooled to −15° C. Isobutylchloroformate (90 µl) was subsequently added and the mixture was allowed to stir for 15 min at −15° C. 2-(N-benzyloxycarbonylmethyl)lysinyl-(4,5-dimethyl)-thiazole (328 mg) was dissolved in dry dimethylformamide (5 ml) and added dropwise to the cold mixed anhydride solution, maintaining the pH at 8.5 by addition of ethyl diisopropyl amine. The reaction mixture was stirred for 60 min at −15° C. The reaction mixture poored into ethyl acetate and successively washed with 0.5M hydrogen chloride solution, water, 5% sodium bicarbonate-solution and brine, dried over sodium sulphate and concentrated in vacuo to yield 658 of the crude title compound.

TLC: $R_f$=0.95, silica gel, ethyl acetate/pyridine/acetic acid/water=163/20/6/11 v/v %.

(1) 2-(N-Carboxymethyl-D-cyclohexylalanyl-prolyl-lysinyl)-4,5-diiethylthlazole 2-(N-(t-Butyloxycarbonylmethyl)-N-Boc-D-cyclohexylalanyl-proly-lysinyi(Cbz))-4,5-dimethylthiazole (650 mg) was treated with trifluoroacetic acid/thioanisole (10 ml) for 4 h at room temperature. The reaction mixture was concentrated in vacuo and the residue dissolved in water and directly charged onto a preparative HPLC DeltaPak RP-$C_{18}$ using a gradient elution system of 20% A/70% B/10% C to 20% A/30% B/50% C over 45 min at a flow rate of 50 ml/min (A: 0.5M phosphate buffer pH 2.1, B: water, C: acetonitril/water=6/4). Yield: 220 mg of the title compound.
$R_t$(LC): 38.10 min, 20% A/80% B to 20% A/20% B/60% C in 40 min.

EXAMPLE 2

2-(N-Carboxymethyl-D-cyclohexylalanyl-prolyl-lysinyl)-4-phenylthiazole

The title compound was prepared according a similar manner as described in example 1 starting with 2-amino-4-phenylthiazole. Yield: 275 mg.
$R_t$(LC): 24.84 min, 20% A/60% B/20% C to 20% A/80% C in 30 min.

EXAMPLE 3

2-(N-Carboxymethyl-D-cyclohexylalanyl-prolyl-lysinyl)-5-methylthiazole

The title compound was prepared according a similar manner as described in example 1 starting with 2-amino-5-methylthiazole. Yield: 110 mg.
$R_t$(LC): 34.54 min, 20% A/80% B to 20% A/20% B/60% C in 40 min.

EXAMPLE 4

2-(N-Carboxymethyl-D-cyclohexylalanyl-prolyl-lysinyl)-4-methylthiazole

The title compound was prepared according a similar manner as described in example 1 starting with 2-amino-4-methylthiazole. Yield: 166 Ing.
$R_t$(LC): 34.41 min, 20% A/80% B to 20% A/20% B/60% C in 40 min.

EXAMPLE 5

2-(N-Carboxymethyl-D-cyclohexylalanyl-prolyl-lysinyl($CH_3$))-thiazole (a) Boc-Lys(Methyl)(Cbz)-OH The pH of a solution of H-Lys(Methyl)-OH.HCl (2 g), copper (II) sulfate pentahydrate (1.32 g) and benzyloxycarbonyloxysuccinimide (2.53 g) was adjusted to 10–10.5 with 2M sodium hydroxide-solution. The mixture was stirred for 16 h at room temperature. The precipitate formed was collected and washed well with water. The filtercake was suspended in dioxane (10 ml) and the pH adjusted to 12.5 with 2M sodium hydroxide-solution and di-t-butyl carbonate (2.22 g) was added. The mixture was stirred for 3 h at room temperature. The precipitate was collected and washed with dioxane. The filtrate was diluted with water and the pH was adjusted to 2.5. Extraction was performed with dichloromethane. The combined organic layers were washed with water dried on anhydrous sodium sulfate and evaporated to dryness and gave 4.43 g of a oil.

(b) 2-(N-Carboxymethyl-D-cyclohexylalanyl-prolyl-lysinyl($CH_3$))-thiazole

The title compound was prepared according a similar manner as described in example 1 starting with 2-bromothiazole and Boc-Lys(Methyl)(Cbz)-OH. Yield: 207 mg.
$R_t$(LC): 32.57 min, 20% A/80% B to 20% A/20% B/60% C in 40 min.

EXAMPLE 6

2-($H_2$NCO-$CH_2$-D-Cha-Pro-Lys)-thiazole.

(a). 2-(H-D-Cha-Pro-Lys(Cbz))-thiazole.TFA.

Boc-D-Cha-Pro-Lys(Cbz)-(2-thiazolyl) was prepared according to the procedure described in example 1. Of this tripeptide, 0.70 g was dissolved in 5 ml trifluoroacetic acid/dichloromethane 1/1 and the solution was stirred for 1 h at room temperature. The solution was evaporated to dryness under reduced pressure and coevaporated three times with toluene. Yield: quantitative, oil, used immediately for the next step.

TLC: Rf=0.30, silica gel, ethyl acetate/pyridine/acetic acid/water=163/20/6/11.

(b). 2-(($H_2$NCO-$CH_2$)-D-Cha-Pro-Lys(Cbz))-thiazole.

H-D-Cha-Pro-Lys(Cbz)-(2-thiazolyl).TFA (0.7 g) was dissolved in 12 ml dry acetonitrile and 93 mg of 2-chloroacetamide and 46 mg of 2-iodoacetamide was added. The pH was adjusted to approx. 8.5 with diisopropyl ethylamine and the reaction mixture was stirred at room temperature for 48 h. The solution was concentrated in vacuo, dissolved in ethylacetate and washed with water, 5% sodium thiosulphate solution and brine. The organic layer was again concentrated in vacuo after being dried on magnesium sulphate. The residue was chromatographed on silica using ethyl acetate/methanol 95/5 as eluent. This yielded 224 mg of the desired tripeptide.

TLC: Rf=0.8, silica gel, ethyl acetate/methanol=9/1.

(c). 2-($H_2$NCO-$CH_2$-D-Cha-Pro-Lys)-thiazole.

The removal of tile protective group and the HPLC purification were performed in an analogous procedure as described for example 1. Yield: 70 mg.

Rt (LC): 31.01 min, 20% A,80% B to 20% A, 20% B and 60% C in 40 min.

EXAMPLE 7

The following examples can also be prepared using the procedures as herein described.

2-(HOOC-$CH_2$-D-Cha-Pro-Lys)-4-(COOEt)thiazole
2-(HOOC-$CH_2$-D-Cha-Pro-Acg)-4-(COOEt)thiazole
2-(HOOC-$CH_2$-D-Cha-Pro-Lys)-6-fluorbenzothiazole
2-(HOOC-$CH_2$-D-Cha-Pro-Acg)-6-fluorbenzothiazole
2-(HOOC-$CH_2$-D-Cha-Pro-Acg)-4,5-dimethylthiazole
2-(HOOC-$CH_2$-D-Cha-Pro-Acg)-4-phenylthiazole
2-(HOOC-$CH_2$-D-Cha-Pro-Acg)-5-methylthiazole
2-(HOOC-$CH_2$-D-Cha-Pro-Acg)-4-methylthiazole
2-($H_2$NCO-$CH_2$-D-Cha-Pro-Acg)-thiazole
2-(HOOC-$CH_2$-D-Cha-Pro-Lys)-benzoxazole
2-(HOOC-$CH_2$-D-Cha-Pro-Acg)-benzoxazole

We claim:

1. A compound having the formula I $$R^1NH-CHR^2-C(O)-A-B-X \qquad (I)$$

wherein $R^1$ is -(1–6C)alkylene-COOH or -(1–6C)alkylene-$CONH_2$;

$R^2$ is a side chain of a hydrophobic D-amino acid;

A is an amino acid selected from proline, optionally containing a second heteroatom selected from N, O, or S, and optionally substituted with (1–6C)alkyl, (1–6C) alkoxy or halogen, 2-azetidine carboxylic acid, pipecolinic acid, octahydroindole-2-carboxylic acid or valine;

B is lysine, 3- or 4-aminocyclohexylglycine or ω-(1–6C) alkyl-lysine; and

X is a heterocycle selected from 2-thiazole, 2-thiazoline, 2-benzothiazole, 2-oxazole, 2-oxazoline, 2-benzoxazole, 2-imidazole and 2-benzimidazole, which heterocycles are optionally substituted with one or more substituents selected from (1–6C)alkyl, (1–6C) alkoxy, oxo, hydroxy, halogen, phenyl, —C(O)O—(1–6C)alkyl or amido;

or a pharmaceutically acceptable salt thereof.

2. The compound of claim 1, wherein B is lysine.

3. The compound of claim 1, wherein A is proline.

4. The compound of claim 1, wherein $R^1$ is —$CH_2COOH$.

5. The compound of claim 1, wherein X is a substituted heterocycle.

6. A pharmaceutical composition comprising the compound of any one of claims 1–5 and pharmaceutically suitable auxiliaries.

7. The compound of claim 2, wherein A is proline.

8. The compound of claim 2, wherein $R^1$ is —$CH_2COOH$.

9. The compound of claim 7, wherein $R^1$ is —$CH_2COOH$.

10. The compound of claim 2, wherein X is a substituted heterocycle.

11. The compound of claim 3, wherein X is a substituted heterocycle.

12. The compound of claim 4, wherein X is a substituted heterocycle.

13. The compound of claim 7, wherein X is a substituted heterocycle.

14. The compound of claim 8, wherein X is a substituted heterocycle.

15. The compound of claim 9, wherein X is a substituted heterocycle.

16. A pharmaceutical composition, comprising the compound of any one of claims 7–15 and pharmaceutically acceptable auxiliaries.

17. A method for treating or preventing thrombin-mediated and thrombin-associated conditions, comprising administering a thrombin inhibiting effective amount of a composition according to claim 6 to a patient.

18. A method for treating or preventing thrombin-mediated and thrombin-associated conditions, comprising administering a thrombin inhibiting effective amount of a composition according to claim 16 to a patient.

19. The method of claim 17, wherein the composition is administered parenterally or enterally.

20. The method of claim 18, wherein the composition is administered parenterally or enterally.

21. The method of claim 19, wherein a daily dosage of 0.001 to 100 mg per kg body weight is administered.

22. The method of claim 20, wherein a daily dosage of 0.001 to 100 mg per kg body weight is administered.

23. A process of making a pharmaceutical composition, comprising mixing the compound of any one of claims 1–5 with pharmaceutically acceptable auxiliaries.

24. A process of making a pharmaceutical composition, comprising mixing the compound of any one of claims 7–15 with pharmaceutically acceptable auxiliaries.

25. The process of claim 23, further comprising compressing the resulting mixture into solid dosage units.

26. The process of claim 24, further comprising compressing the resulting mixture into solid dosage units.

* * * * *